US006871646B2

(12) United States Patent
Keane et al.

(10) Patent No.: US 6,871,646 B2
(45) Date of Patent: Mar. 29, 2005

(54) DE-AGGLOMERATOR FOR BREATH-ACTUATED DRY POWDER INHALER

(75) Inventors: Laurence Keane, Aldwick (GB); David O'Leary, Essex (GB)

(73) Assignee: Norton Healthcare Ltd., London (GB)

( * ) Notice: Subject to any disclaimer, the term of this patent is extended or adjusted under 35 U.S.C. 154(b) by 0 days.

(21) Appl. No.: 10/837,004

(22) Filed: Apr. 30, 2004

(65) Prior Publication Data

US 2004/0200475 A1 Oct. 14, 2004

Related U.S. Application Data

(62) Division of application No. 09/888,281, filed on Jun. 23, 2001, now Pat. No. 6,748,947.
(60) Provisional application No. 60/213,668, filed on Jun. 23, 2000, provisional application No. 60/213,667, filed on Jun. 23, 2000, and provisional application No. 60/213,382, filed on Jun. 23, 2000.

(51) Int. Cl.7 ........................ A65D 83/06; A61M 15/08; A61M 15/00; A61M 16/00
(52) U.S. Cl. ........................... 128/203.15; 128/203.21; 128/203.18
(58) Field of Search ...................... 128/203.15, 204.24, 128/204.25, 204.26, 203.21, 203.18, 203.12, 203.14

(56) References Cited

U.S. PATENT DOCUMENTS

| | | | |
|---|---|---|---|
| 3,795,244 A | 3/1974 | Lax et al. | |
| 4,446,862 A | 5/1984 | Baum et al. | |
| 4,739,754 A | 4/1988 | Shaner | |
| 5,458,135 A | 10/1995 | Patton et al. | |
| 5,678,538 A | 10/1997 | Drought | |
| 5,829,434 A | 11/1998 | Ambrosio et al. | |
| 5,947,117 A | 9/1999 | Herold et al. | |
| 6,055,980 A | 5/2000 | Mecikalski et al. | |

(Continued)

FOREIGN PATENT DOCUMENTS

| | | |
|---|---|---|
| JP | 11299891 | 11/1999 |
| WO | WO97/12639 | 4/1997 |

(Continued)

*Primary Examiner*—Henry Bennett
*Assistant Examiner*—Kathryn Odland
(74) *Attorney, Agent, or Firm*—McDermott Will & Emery LLP

(57) ABSTRACT

A de-agglomerator is provided for use with a breath-actuated dry powder inhaler for breaking up aggregates and micronizing particles of dry powder prior to inhalation of the powder by a patient using the inhaler. The de-agglomerator includes an inner wall defining a swirl chamber extending along an axis from a first end to a second end, a dry powder supply port, an inlet port, and an outlet port. The supply port is in the first end of the swirl chamber for providing fluid communication between a dry powder delivery passageway of an inhaler and the first end of the swirl chamber. The inlet port is in the inner wall of the swirl chamber adjacent to the first end of the swirl chamber and provides fluid communication between a region exterior to the de-agglomerator and the swirl chamber. The outlet port provides fluid communication between the second end of the swirl chamber and a region exterior to the de-agglomerator, whereby a breath induced low pressure at the outlet port causes air flows into the swirl chamber through the dry powder supply port and the inlet port. The air flows collide with each other and with the wall of the swirl chamber prior to exiting through the outlet port, such that any powder entrained in the air flows is broken down and micronized. The de-agglomerator further includes vanes at the first end of the swirl chamber for creating additional collisions and impacts of entrained powder.

6 Claims, 3 Drawing Sheets

U.S. PATENT DOCUMENTS

| | | | |
|---|---|---|---|
| 6,062,214 A | 5/2000 | Howlett | |
| 6,065,472 A | 5/2000 | Anderson et al. | |
| 6,073,629 A | 6/2000 | Hardy et al. | |
| 6,095,141 A | 8/2000 | Armer et al. | |
| 6,116,239 A | 9/2000 | Volgyesi | |
| 6,237,591 B1 | 5/2001 | Jackson | |
| 6,257,232 B1 | 7/2001 | Andersson et al. | |
| 6,347,629 B1 | 2/2002 | Braithwaite | |
| 6,367,471 B1 | 4/2002 | Genosar et al. | |
| 6,408,846 B1 | 6/2002 | Ohki et al. | |
| 6,418,926 B1 * | 7/2002 | Chawla | 128/203.12 |
| 6,681,768 B2 * | 1/2004 | Haaije de Boer et al. | 128/203.15 |
| 6,748,947 B2 * | 6/2004 | Keane et al. | 128/203.15 |
| 2002/0073997 A1 * | 6/2002 | Keane et al. | 128/203.21 |
| 2003/0015195 A1 * | 1/2003 | Haaije de Boer et al. | 128/203.15 |

FOREIGN PATENT DOCUMENTS

| | | |
|---|---|---|
| WO | WO99/15217 | 4/1999 |
| WO | WO99/20331 | 4/1999 |
| WO | WO99/27987 | 6/1999 |

* cited by examiner

DE-AGGLOMERATOR FOR BREATH-ACTUATED DRY POWDER INHALER

CROSS-REFERENCE TO RELATED APPLICATIONS

The present application is a divisional of now abandoned U.S. patent application Ser. No. 09/888,281, filed on Jun. 23, 2001 now U.S. Pat. No. 6,748,947, which claims priority to provisional U.S. patent application Ser. No. 60/213,668, filed Jun. 23, 2000 (entitled "Breath-Actuated Dry Powder Inhaler"), provisional U.S. patent application Ser. No. 60/213,667, filed Jun. 23, 2000 (entitled "Pre-Metered Dose Magazine for Breath-Actuated Dry Powder Inhaler"), and now abandoned provisional U.S. patent application Ser. No. 60/213,382, filed Jun. 23, 2000 (entitled "De-Agglomerator for Breath-Actuated Dry Powder Inhaler"). Each of these applications is assigned to the assignee of the present disclosure and incorporated herein by reference.

FIELD OF THE INVENTION

The invention relates to a breath-actuated dry powder inhaler for administering dry powder medicament, or a dry powder composition of medicament mixed with a suitable carrier agent, e.g., lactose, to a patient. More particularly, the present disclosure relates to a de-agglomerator for a breath-actuated dry powder inhaler and a method of de-agglomerating a dry powder medicament or a dry powder composition of medicament and a suitable carrier.

BACKGROUND OF THE INVENTION

Metered dose medicament inhalers are well known for dispensing medicament to the lungs of a patient. Some previous inhalers have comprised a pressurized aerosol dispensing container, wherein the aerosols contain gas propellants in which the powdered medicament is suspended. Upon actuation, the aerosol contents are expelled, through a metering valve, and into the lungs of the patient. However, it is now known that some aerosol propellants, including those used in metered dose inhalers, can cause depletion of the ozone layer in the atmosphere. In addition, such aerosol systems are not suitable for all patients.

Several types of non-aerosol, breath actuated dry powder inhalers have therefore been provided. For example, U.S. Pat. No. 5,503,144 to Bacon, which is assigned to the assignee of the present disclosure and incorporated herein by reference, shows a breath-actuated dry-powder inhaler. The device includes a dry powder reservoir for containing a dry powdered medicament, a metering chamber for removal of the powdered medicament from the reservoir in discrete amounts, and an air inlet for entraining the removed powdered medicament through a mouth piece upon patient inhalation.

Regardless of whether an aerosol or non-aerosol inhaler is used, it is of utmost importance that particles of the dispensed dry powder medicament be small enough to ensure the adequate penetration of the medicament into the bronchial region of a patient's lungs during inhalation. However, because the dry powder medicament is composed of very small particles, and often provided in a composition including a carrier such as lactose, non-defined agglomerates or aggregates of the medicament form at random prior to being dispensed. It has therefore been found preferably to provide breath-actuated dry powder inhalers with means for breaking down the agglomerates of medicament or medicament and carrier before inhalation of the medicament.

Accordingly, there is desired an improved dry powder inhaler and, in particular, an improved breath-actuated dry powder inhaler. There is also desired a de-agglomerator for a breath-actuated dry powder inhaler and method for breaking down agglomerates of medicament, or medicament and carrier, before inhalation of the medicament by a patient.

SUMMARY OF THE INVENTION

The present disclosure accordingly provides a de-agglomerator for use with a breath-actuated dry powder inhaler for breaking up aggregates and micronizing particles of dry powder prior to inhalation of the powder by a patient. The de-agglomerator includes an inner wall defining a swirl chamber extending along an axis from a first end to a second end, a dry powder supply port, an inlet port, and an outlet port.

The supply port is in the first end of the swirl chamber for providing fluid communication between a dry powder delivery passageway of an inhaler and the first end of the swirl chamber. The inlet port is in the inner wall of the swirl chamber adjacent to the first end of the swirl chamber and provides fluid communication between a region exterior to the de-agglomerator and the swirl chamber. The outlet port provides fluid communication between the second end of the swirl chamber and a region exterior to the de-agglomerator.

A breath induced low pressure at the outlet port causes air flows into the swirl chamber through the dry powder supply port and the inlet port. The air flows collide with each other and with the wall of the swirl chamber prior to exiting through the outlet port, such that any powder entrained in the air flows is broken down and micronized. The de-agglomerator further includes vanes at the first end of the swirl chamber for creating additional collisions and impacts of entrained powder.

The present disclosure also provides a method of de-agglomerating dry powder from a breath-actuated dry powder inhaler, prior to inhalation of the dry powder by a patient: The method includes directing a first breath-actuated air flow for entraining a dry powder from an inhaler into a first end of a chamber extending longitudinally between the first end and a second end, the first air flow directed in a longitudinal direction.

A second breath-actuated airflow is directed in a substantially transverse direction into the first end of the chamber such that the air flows collide and substantially combine. Then, a portion of the combined air flows is deflected in a substantially longitudinal direction towards a second end of the chamber, and a remaining portion of the combined air flows is directed in a spiral path towards the second end of the chamber. All the combined air flows and any dry powder entrained therein are then delivered from the second end of the chamber to a patient's mouth.

The de-agglomerator and method of de-agglomerating according to the present disclosure, therefore, ensure that particles of dry powder are small enough for adequate penetration of the powder into a bronchial region of a patient's lungs during inhalation of the dry powder by the patient.

Further features and advantages of the presently disclosed de-agglomerator and method of de-agglomerating will become more readily apparent to those having ordinary skill in the art to which the present disclosure relates from the following detailed description and attached drawings.

BRIEF DESCRIPTION OF THE DRAWINGS

So that those having ordinary skill in the art will more readily understand how to construct a de-agglomerator in accordance with the present disclosure, a preferred embodiment is described in detail below with reference to the drawing figures wherein.

DESCRIPTION OF THE PREFERRED EMBODIMENT

Figure 1:
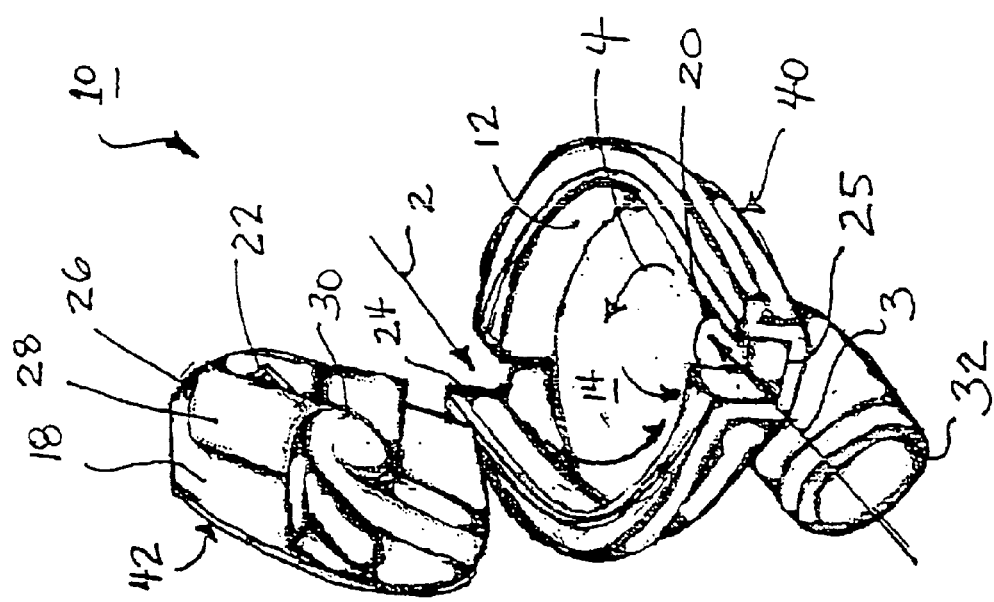
FIG. 1 is an exploded isometric view of a de-agglomerator according to the present disclosure.

Referring to FIGS. 1 through 6, the present disclosure provides a de-agglomerator 10 for breaking down agglomerates of medicament, or medicament and carrier, before inhalation of the medicament by a patient. Although not shown, the de-agglomerator 10 is for use with a breath-actuated dry powder inhaler including a dry powder delivery passageway and a dry powder reservoir for exposing a predetermined amount of dry powder to the dry powder delivery passageway. Preferably, the dry powder delivery passageway of the inhaler will include a venturi adjacent the dry powder reservoir such that an air flow passing therethrough will entrain dry powder in the reservoir. Examples of breath-actuated dry powder inhalers utilizing the presently disclosed de-agglomerator 10 are shown in co-pending provisional U.S. patent application Ser. No. 60/213,668, filed Jun. 23, 2000 (entitled "Breath-Actuated Dry Powder Inhaler"), provisional U.S. patent application Ser. No. 60/213,669, filed Jun. 23, 2000 (entitled "Pre-Metered Dose Magazine for Breath-Actuated Dry Powder Inhaler"). Both co-pending applications are assigned to the assignee of the present disclosure and have been incorporated herein by reference.

In general, the presently disclosed de-agglomerator 10 includes an inner wall 12 defining a swirl chamber 14 extending along an axis A from a first end 18 to a second end 20. The swirl chamber 14 includes circular cross-sectional areas arranged transverse to the axis A, that decrease from the first end 18 to the second end 20 of the swirl chamber 14, such that any air flow traveling from the first end of the swirl chamber to the second end will be constricted and at least in part collide with the inner wall 12 of the chamber. Preferably, the cross-sectional areas of the swirl chamber 14 decrease monotonically. In addition, the inner wall 12 is preferably convex, i.e., arches inwardly towards the axis A, as shown best in FIG. 6.

Figure 3:
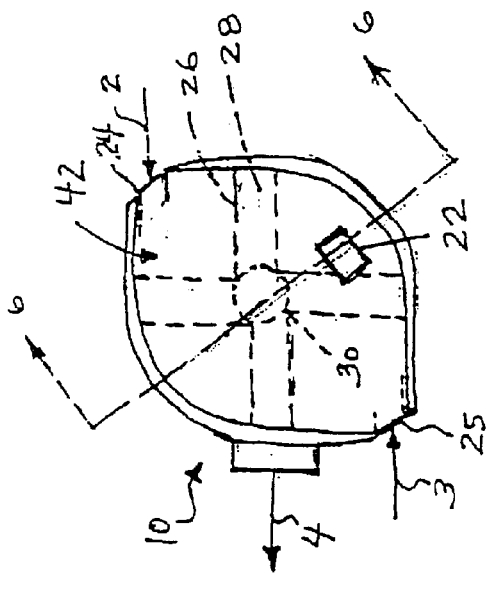
FIG. 3 is a top plan view of the de-agglomerator of FIG. 1.
Figure 4:
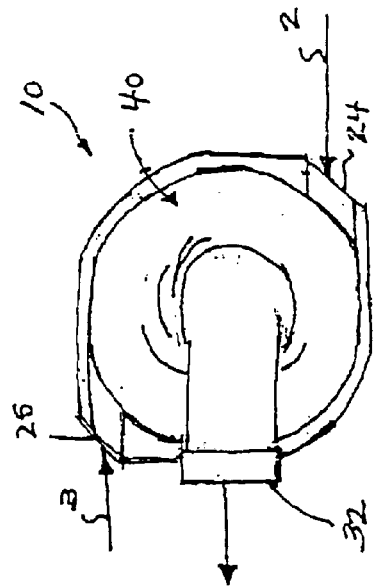
FIG. 4 is a bottom plan view of the de-agglomerator of FIG. 1.
Figure 2:
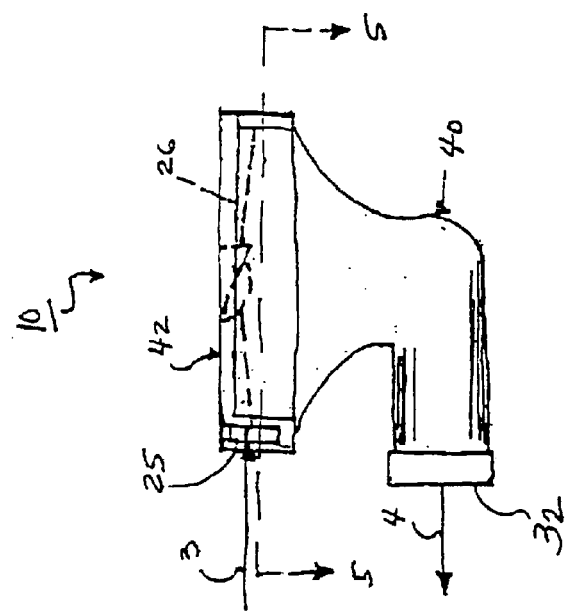
FIG. 2 is a side elevation view of the de-agglomerator of FIG. 1.
Figure 6:
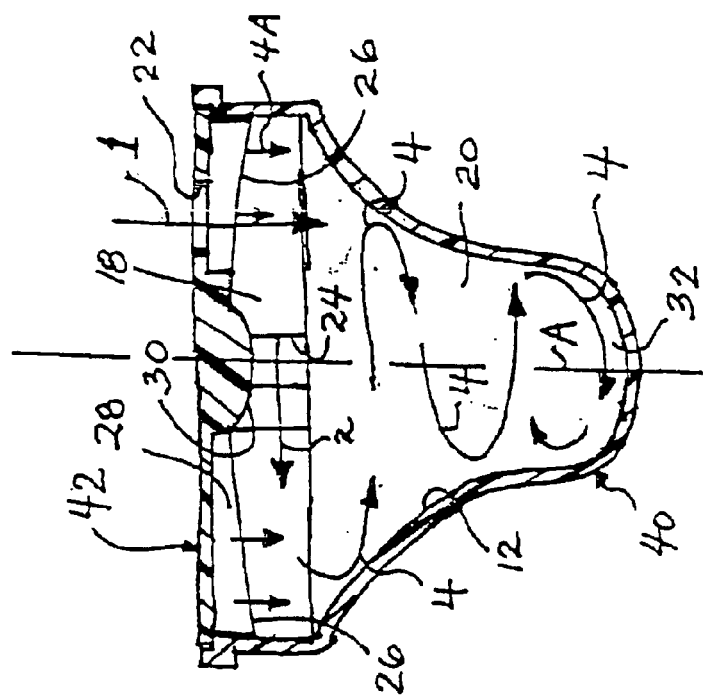
FIG. 6 is a sectional view of the de-agglomerator of FIG. 1 taken along line 6—6 of FIG. 3.
Figure 5:
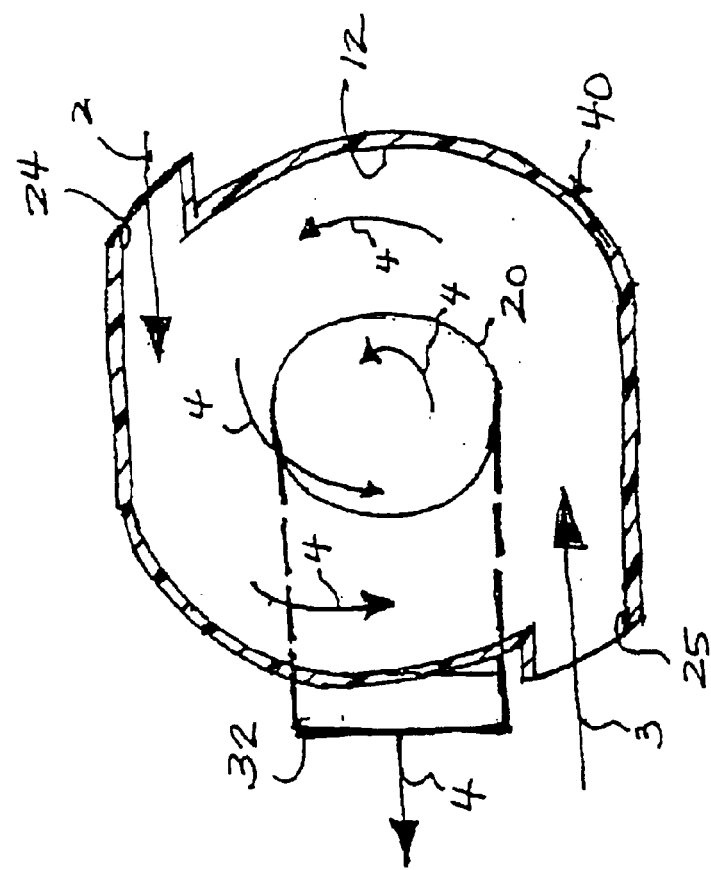
FIG. 5 is a sectional view of the de-agglomerator of FIG. 1 taken along line 5—5 of FIG. 2.

As shown in FIGS. 1, 3 and 6, the de-agglomerator 10 also includes a dry powder supply port 22 in the first end 18 of the swirl chamber 14 for providing fluid communication between a dry powder delivery passageway of an inhaler and the first end 18 of the swirl chamber 14. Preferably, the dry powder supply port 22 faces in a direction substantially parallel with the axis A such that an air flow, illustrated by arrow 1 in FIG. 6, entering the chamber 14 through the supply port 22 is at least initially directed parallel with respect to the axis A of the chamber.

Referring to FIGS. 1 through 6, the de-agglomerator 10 additionally includes at least one inlet port 24 in the inner wall 12 of the swirl chamber 14 adjacent to or near the first end 18 of the chamber providing fluid communication between a region exterior to the de-agglomerator and the first end 18 of the swirl chamber 14. Preferably, the at least one inlet port comprises two diametrically opposed inlet ports 24, 25 that extend in a direction substantially transverse to the axis A and substantially tangential to the circular cross-section of the swirl chamber 14. As a result, air flows, illustrated by arrows 2 and 3 in FIGS. 1 and 5, entering the chamber 14 through the inlet ports are at least initially directed transverse with respect to the axis A of the chamber and collide with the air flow 1 entering through the supply port 22 to create turbulence. The combined air flows, illustrated by arrow 4 in FIGS. 5 and 6, then collide with the inner wall 12 of the chamber 14, form a vortex, and create additional turbulence as they move towards the second end 20 of the chamber.

Referring to FIGS. 1–3 and 6, the de-agglomerator 10 includes vanes 26 at the first end 18 of the swirl chamber 14 extending at least in part radially outwardly from the axis A of the chamber. Each of the vanes 26 has an oblique surface 28 facing at least in part in a direction transverse to the axis A of the chamber. The vanes 26 are sized such that at least a portion 4A of the combined air flows 4 collide with the oblique surfaces 28, as shown in FIG. 6. Preferably, the vanes comprise four vanes 26, each extending between a hub 30 aligned with the axis A and the wall 12 of the swirl chamber 14.

As shown in FIGS. 1 through 6, the de-agglomerator 10 further includes an outlet port 32 providing fluid communication between the second end 20 of the swirl chamber 14 and a region exterior to the de-agglomerator. The outlet port 32 acts as a mouthpiece for a patient using an inhaler incorporating the de-agglomerator 10. A breath induced low pressure at the outlet port 32 causes the air flow 1 through the supply port 22 and the air flows 2, 3 through the inlet ports and draws the combined air flow 4 through the swirl chamber 14. The combined air flow 4 then exits the de-agglomerator through the outlet port 32. Preferably the outlet port 32 extends substantially transverse to the axis A, such that the air flow 4 will collide with an inner wall of the outlet port 32 and create further turbulence.

During use of the de-agglomerator 10 in combination with a breath-actuated dry powder inhaler including a dry powder delivery passageway and a dry powder reservoir for exposing a predetermined amount of dry powder to the delivery passageway, patient inhalation at the outlet port 32 causes air flows 1, 2, 3 to enter through, respectively, the dry powder supply port 22 and the inlet ports. Although not shown, the air flow 1 through the supply port 22 entrains the dry powder into the swirl chamber 14. The air flow 1 and entrained dry powder are directed by the supply port 22 into the chamber in a longitudinal direction, while the air flows 2, 3 from the inlet ports are directed in a transverse direction, such that the air flows collide and substantial combine.

A portion of the combined air flow 4 and the entrained dry powder then collide with the oblique surfaces 28 of the vanes 26 causing particles and any agglomerates of the dry powder to impact against the oblique surfaces and collide with each other. The geometry of the swirl chamber 14 causes the combined air flow 4 and the entrained dry powder to follow a turbulent, spiral path, or vortex, through the chamber. As will be appreciated, the decreasing cross-sections of the swirl chamber 14 continuously changes the direction and increases the velocity of the spiraling combined air flow 4 and entrained dry powder. Thus, particles and any agglomerates of the dry powder constantly impact against the wall 12 of the swirl chamber 14 and collide with each other, resulting in a mutual grinding or shattering action between the particles and agglomerates. In addition, particles and agglomerates deflected off the oblique surfaces 28 of the vanes 26 cause further impacts and collisions. The constant impacts and collisions cause any agglomerates to break into additional particles, and cause the particles to be substantially micronized.

Upon exiting the swirl chamber 14, the direction of the combined air flow 4 and the entrained dry powder is again changed to a transverse direction with respect to the axis A, through the outlet port 32. The combined air flow 4 and the entrained dry powder retain a swirl component of the flow, such that the air flow 4 and the entrained dry powder spirally swirls through the outlet port 32. Since the micronized powder and any remaining agglomerates maintain the swirl imparted from swirl chamber 14, the swirling flow causes additional impacts in the outlet port 32 so as to result in further breaking up of any remaining agglomerates prior to being inhaled by a patient.

The de-agglomerator according to the present disclosure, therefore, ensures that particles of the dry powder are small enough for adequate penetration of the powder into a bronchial region of a patient's lungs during inhalation.

As shown in FIGS. 1 through 6, the de-agglomerator is preferably assembly from two pieces: a cup-like base 40 and a cover 42. The base 40 and the cover 42 are connected to form the swirl chamber 14. The cup-like base 40 includes the wall 12 and the second end 20 of the chamber and defines the outlet port 32. The base 40 also includes the inlet ports of the swirl chamber 14. The cover 42 forms the vanes 26 and defines the supply port 22.

The base 40 and the cover 42 of the de-agglomerator are preferably manufactured from a plastic such as polypropylene, acetal or moulded polystyrene, but may be manufactured from metal or another suitable material. Preferably, the cover 42 includes an anti-static additive, so that dry powder will not cling to the vanes 26. The base 40 and the cover 42 are then connected in a manner that provides an air tight seal between the parts. For this purpose heat or cold sealing, laser welding or ultra sonic welding could be used, for example.

It should be understood that the foregoing detailed description and preferred embodiment is only illustrative of de-agglomerator according to the present disclosure. Various alternatives and modifications to the presently disclosed de-agglomerator can be devised by those skilled in the art without departing from the spirit and scope of the present disclosure. For example, the de-agglomerator can be provided as a single piece through blow molding. In addition, the de-aggregator can be modified to be used with any inhaler and, in particular, any breath-actuated dry powder inhaler. Accordingly, the present disclosure is intended to embrace all such alternatives and modifications that fall within the spirit and scope of a de-agglomerator and a method of de-agglomerating as recited in the appended claims.

What is claimed is:

1. A method of de-agglomerating dry powder from a breath-actuated dry powder inhaler prior to inhalation of the dry powder by a patient, comprising:

directing a first breath-actuated air flow for entraining a dry powder from an inhaler into a first end of a chamber extending along a longitudinal axis from the first end to a second end, the first air flow directed in a longitudinal direction;

directing a second breath-actuated air flow in a substantially transverse direction into the first end of the chamber such that the first and the second breath-actuated air flows collide and substantially combine;

deflecting a first portion of the combined air flows off vanes non-rotationally fixedly attached to the first end of the chamber and extending at least in part radially outwardly from the axis of the chamber, wherein each of the vanes has an oblique surface facing at least in part in a direction transverse to the axis, such that the first portion of the combined air flows is deflected in a substantially longitudinal direction towards the second end of the chamber;

directing a second portion of the combined air flows in a spiral path towards the second end of the chamber; and delivering all the combined air flows and any dry powder entrained therein through an outlet port in the second end of the chamber to a patient's mouth.

2. A method according to claim 1, wherein the second breath-actuated air flow is directed tangentially into the first end of the chamber.

3. A method according to claim 1, wherein a third breath-actuated airflow is directed in a substantially transverse direction into the first end of the chamber such that the third air flow collides and substantially combines with the first and the second air flows.

4. A method according to claim 1, wherein the combined air flows and any dry powder entrained therein are delivered through the outlet port of the second end of the chamber to a patient's mouth in a substantially transverse direction.

5. A method according to claim 1, wherein the combined air flows are constricted between the first end and the second end of the chamber.

6. A method according to claim 1, wherein the combined air flows are monotonically constricted between the first end and the second end of the chamber.

* * * * *